United States Patent [19]

Akashi

[11] Patent Number: 5,402,199
[45] Date of Patent: Mar. 28, 1995

[54] VISUAL AXIS DETECTING APPARATUS

[75] Inventor: Akira Akashi, Yokohama, Japan

[73] Assignee: Canon Kabushiki Kaisha, Tokyo, Japan

[21] Appl. No.: 133,304

[22] Filed: Oct. 8, 1993

[30] Foreign Application Priority Data

Oct. 16, 1992 [JP] Japan .................................. 4-278723
Oct. 30, 1992 [JP] Japan .................................. 4-316564

[51] Int. Cl.⁶ ......................... G03B 17/00; A61B 3/14
[52] U.S. Cl. .................................................. 354/410
[58] Field of Search ........................... 354/410, 219, 62

[56] References Cited

FOREIGN PATENT DOCUMENTS 1274736 11/1989 Japan .

Primary Examiner—W. B. Perkey
Attorney, Agent, or Firm—Fitzpatrick, Cella, Harper & Scinto

[57] ABSTRACT

This specification discloses a visual axis detecting apparatus provided with means for illuminating an observer's eyeball, first means for detecting the characteristic portion of the image of the observer's eyeball, second means for detecting the corneal reflected image by the illuminating means from the image of the observer's eyeball, means for selecting some corneal reflected image from among the corneal reflected images obtained by the second means, visual axis detecting means for detecting the observer's visual axis from the positional relation between the characteristic portion and the selected corneal reflected image, means for evaluating the state of the detected visual axis, and means for reselecting another corneal reflected image when it is evaluated by the evaluating means that the state of the visual axis is inappropriate.

17 Claims, 11 Drawing Sheets

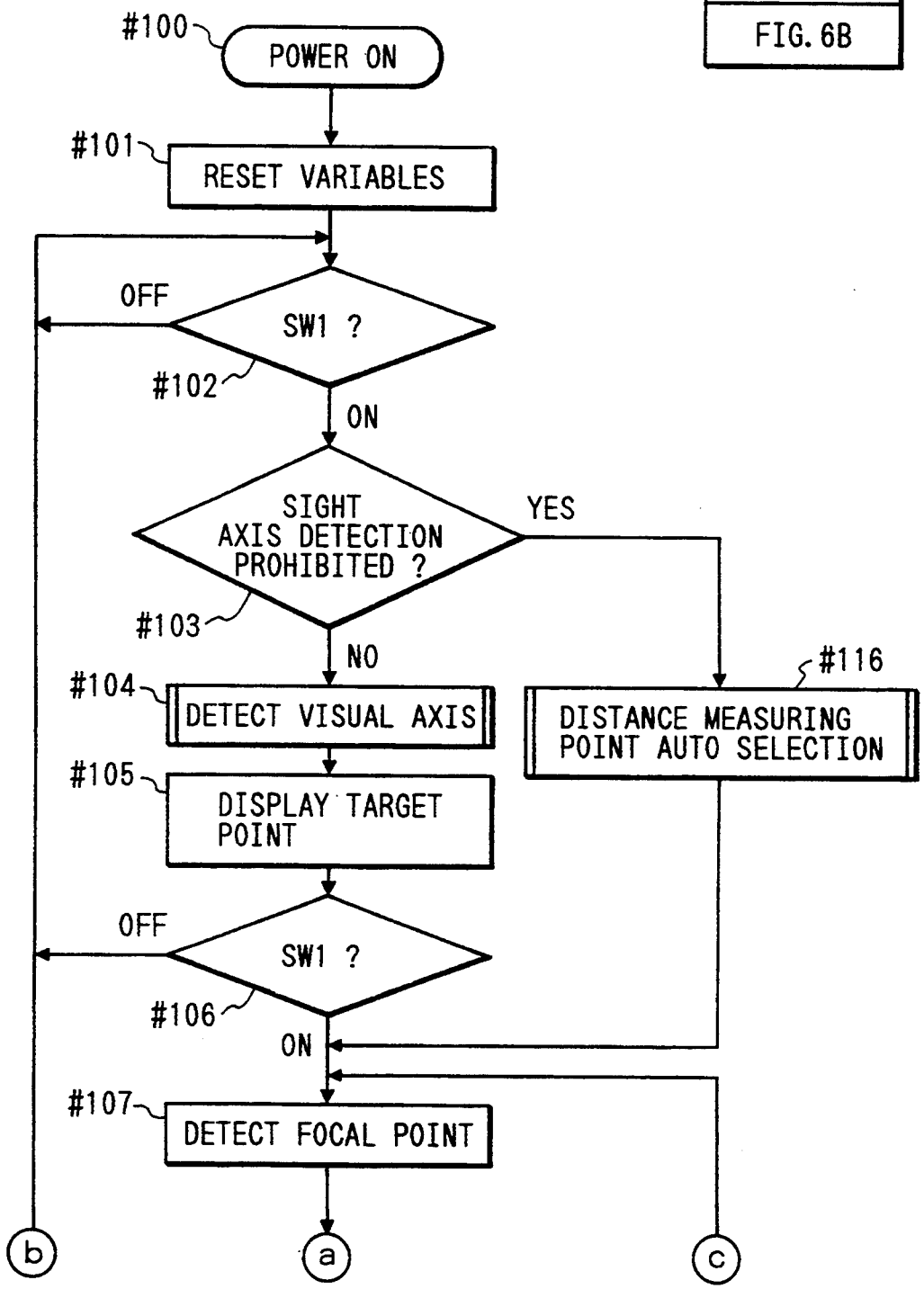
FIG. 6A
FIG. 6
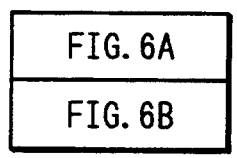

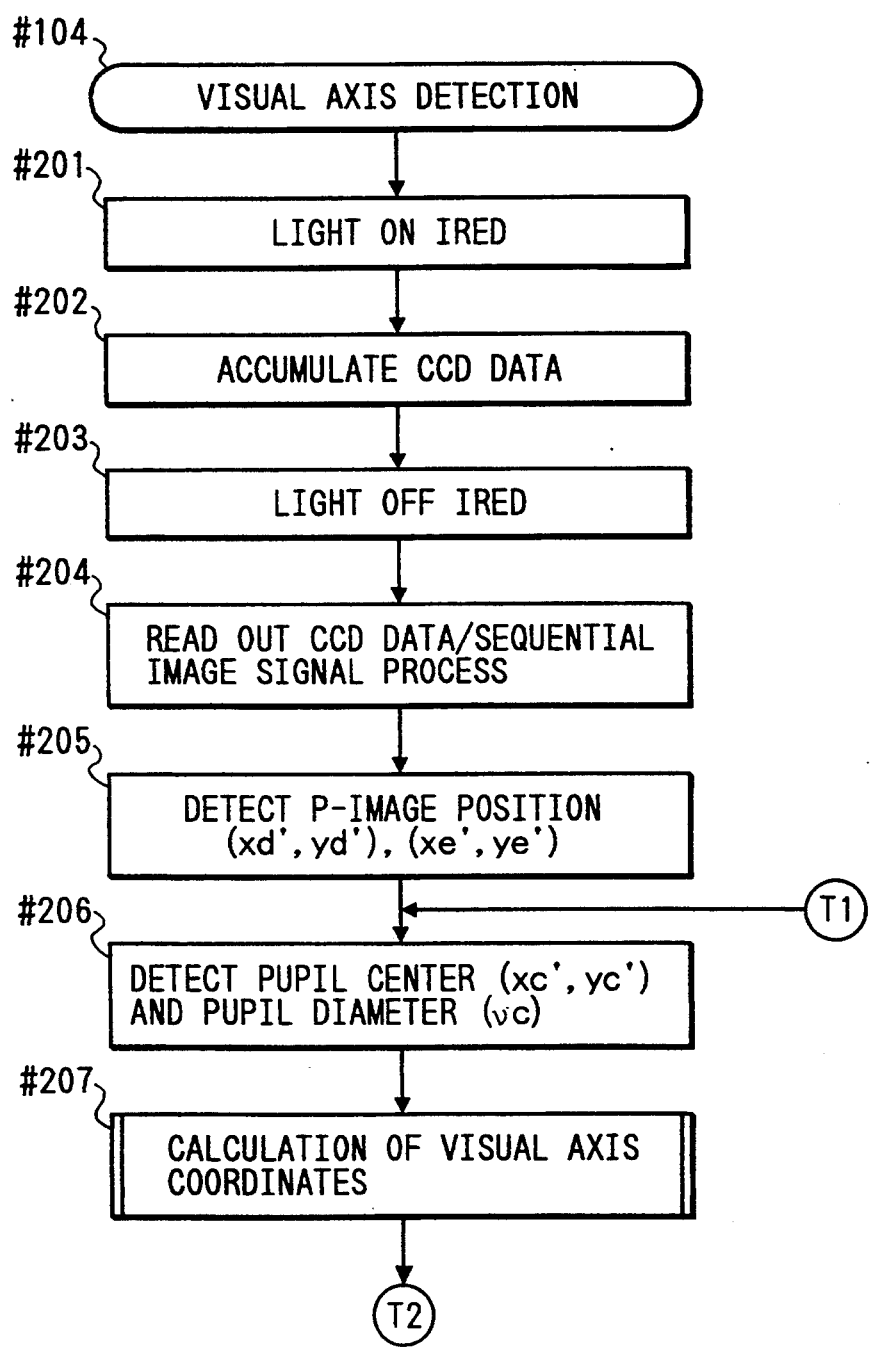

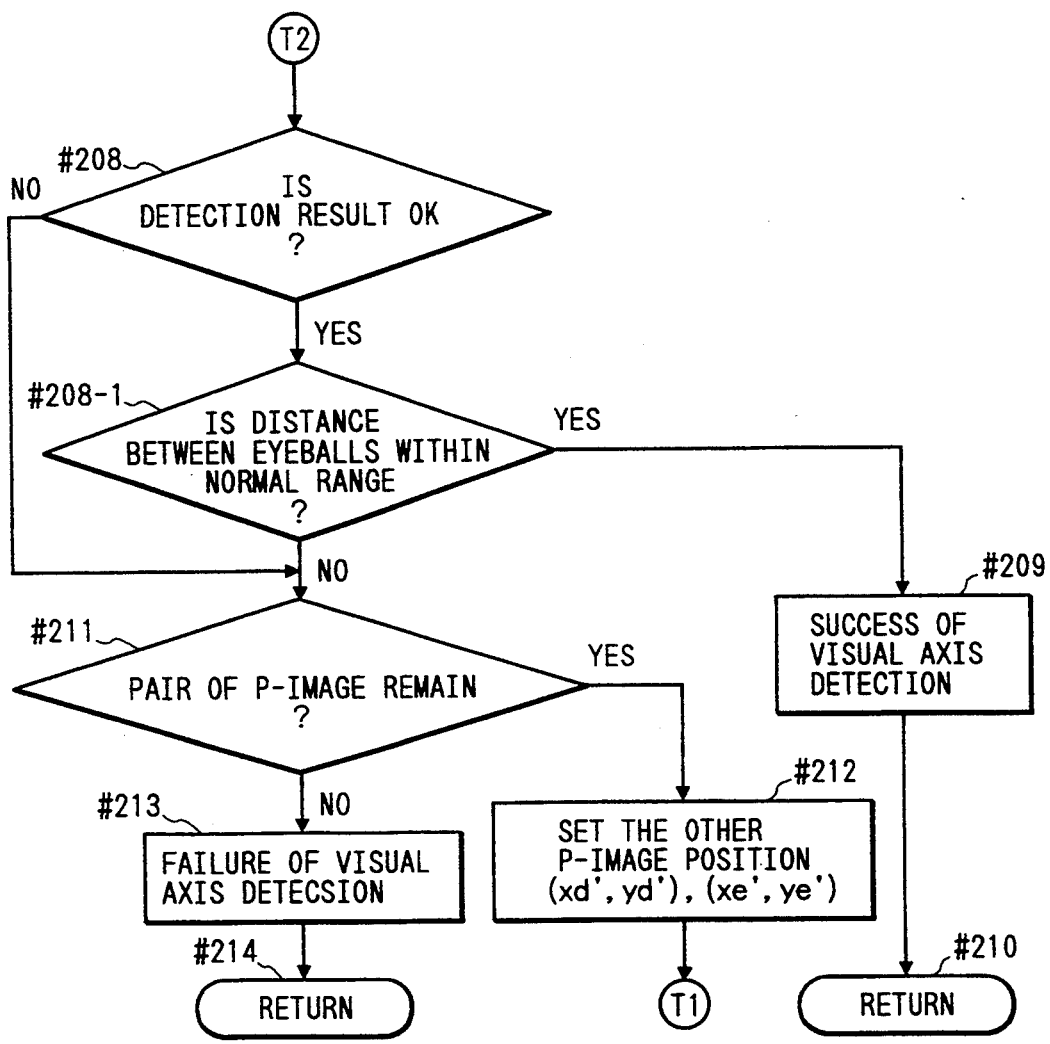

VISUAL AXIS DETECTING APPARATUS

BACKGROUND OF THE INVENTION

1. Field of the Invention

This invention relates to an optical apparatus having visual axis detecting means, and particularly to an optical apparatus having visual axis detecting means for detecting the axis in the direction of a target point being observed by an observer (photographer) through a finder system on an observation surface (focusing screen) on which an object image by a photographing system is formed, i.e., the so-called sight axis (visual axis), by the utilization of the reflected image of the observer's eyeball obtained when the surface of the observer's eyeball is illuminated, and effecting various photographing operations.

2. Related Background Art

There have heretofore been proposed various apparatuses (for example, eye cameras) for detecting what position on the observation surface an observer is observing, i.e., detecting the so-called sight axis (visual axis).

For example, in Japanese Laid-Open Patent Application No. 1-274736, a parallel light beam from a light source is projected onto the front eye part of an observer's eyeball and the sight axis is found by the utilization of the corneal reflected image by reflected light from the cornea and the imaged position of the pupil.

FIG. 10 of the accompanying drawings illustrates the principle of a visual axis detecting method.

FIG. 1A of the accompanying drawings shows an eyeball image in a very usual case where it is projected onto the surface of the image sensor 14 of FIG. 10, and the numeral 60 in FIG. 1B of the accompanying drawings designates an image signal output on a line (I)—(I)'.

In FIG. 1A, the numeral 50 represents the so-called white of the eyeball, the numeral 51 represents the pupil, and the numerals 52a and 52b represent the corneal reflected images of an eyeball illuminating light source.

FIG. 2 of the accompanying drawings shows an example of the eyeball image of a photographer wearing spectacles. The numerals 52a and 52b represent corneal reflected images, and the numerals 53a, 53b, 54a and 54b represent the ghost images of the light source by the spectacle.

The visual axis detecting method will now be described with reference to FIG. 10 and FIGS. 1A and 1B. Infrared light emitting diodes 13a and 13b are disposed substantially symmetrically in Z direction with respect to the optical axis $ax_1$ of a light receiving lens 12, and divergently illuminate the photographer's eyeball.

Infrared light emitted from the infrared light emitting diode 13b illuminates the cornea 16 of the eyeball 15. At this time, the corneal reflected image d by part of the infrared light reflected by the surface of the cornea 16 is condensed by the light receiving lens 12 and is re-imaged at a position d' on an image sensor 14.

Likewise, infrared light emitted from the infrared light emitting diode 13a illuminates the cornea 16 of the eyeball. At this time, the corneal reflected image e by part of the infrared light reflected by the surface of the cornea 16 is condensed by the light receiving lens 12 and is re-imaged at a position e' on the image sensor 14.

Light beams from the end portions a and b of an iris 17 form the images of the end portions a and b on the image sensor 14 through the light receiving lens 12. If the rotation angle $\theta$ of the optical axis $ax_2$ of the eyeball 15 relative to the optical axis $ax_1$ of the light receiving lens 12 is small, when the Z coordinates of the end portions a and b of the iris 17 are Za and Zb, the coordinates Zc of the central position c of the pupil 19 are expressed as $$Zc \simeq (Za+Zb)/2.$$

Also, the Z coordinates of the middle point of corneal reflected images d' and e' and the Z coordinates Zo of the center of curvature O of the cornea 16 coincide with each other and therefore, when the Z coordinates of positions d' and e' at which the corneal reflected images are created are Zd and Ze and the standard distance from the center of curvature O of the cornea 16 to the center C of the pupil 19 is $L_{OC}$ and a coefficient which takes the individual difference relative to the distance $L_{OC}$ into account is A1, the rotation angle $\theta$ of the optical axis $ax_2$ of the eyeball substantially satisfies the following relational expression:

$$(A1 \times L_{OC}) \times \sin\theta \simeq Zc - (Zd+Ze)/2 \qquad (1)$$

Therefore, in a visual axis calculation processing apparatus, by detecting the positions of respective characteristic points (corneal reflected images d, e and the end portions a and b of the iris) projected onto portions of the image sensor as shown in FIG. 1B, the rotation angle $\theta$ of the optical axis $ax_2$ of the eyeball can be found. At this time, expression (1) is rewritten into $$\beta(A1 \times L_{OC}) \times \sin\theta \simeq (Za'+Zb')/2 - (Zd'+Ze')/2 \qquad (2)$$

where $\beta$ is a magnification determined by the position of the eyeball relative to the light receiving lens 12, and is substantially found as a function of the spacing $|Zd'-Ze'|$ between the corneal reflected images. The rotation angle $\theta$ of the eyeball 15 is rewritten into $$\theta \simeq ARCSIN\{(Zc'-Zf)/\beta/(A1 \times L_{OC})\} \qquad (3)$$

where $$Zc' \simeq (Za'+Zb')/2$$

$$Zf \simeq (Zd'+Ze')/2.$$

Now, the sight axis does not coincide with the optical axis $ax_2$ of the photographer's eyeball and therefore, when the rotation angle $\theta$ of the optical axis $ax_2$ of the photographer's eyeball in the horizontal direction is calculated, the angle correction $\delta$ of the optical axis of the eyeball and the sight axis is effected, whereby the photographer's visual axis $\theta H$ in the horizontal direction can be found. When a coefficient which takes the individual difference relative to the correction angle $\delta$ of the optical axis $ax_2$ of the eyeball and the sight axis into account is B1, the photographer's visual axis $\theta H$ in the horizontal direction is found as $$\theta H = \theta \pm (B1 \times \delta) \qquad (4)$$

where as regards the signs $\pm$, when the rightward rotation angle with respect to the photographer is positive, if the photographer's eye looking into the observation apparatus is the left eye, the sign + is selected, and if the photographer's eye looking into the observation apparatus is the right eye, the sign "−" is selected.

Also, in FIG. 10, there is shown an example in which the photographer's eyeball rotates in Z-X plane (for example, a horizontal plane), but detection is likewise possible when the photographer's eyeball rotates in X-Y plane (for example, a vertical plane). However, the component of the photographer's visual axis in the vertical direction coincides with the component $\theta'$ of the optical axis of the visual axis in the vertical direction and therefore, the visual axis $\theta V$ in the vertical direction is $$\theta V = \theta'.$$

Further, from visual axis data $\theta H$ and $\theta V$, the positions (Zn, Yn) on the focusing screen in the finder field the photographer is seeing are found as $$Zn \simeq m \times \theta H$$
$$\simeq m \times [ARCSIN\{Zc' - Zf\}/\beta/(A1 - \times L_{OC})\} \pm (B1 \times \delta)] \quad (5)$$

$$Yn \simeq m \times \theta V,$$

where m is a constant determined by the finder optical system of the camera.

The values of coefficients A1 and B1 for correcting the individual difference of the photographer's eyeball can be found by making the photographer fixate at a target disposed at a predetermined location in the finder of the camera, and making the location of the target and the position of the fixation point calculated in accordance with expression (5) coincident with each other.

The calculations for finding the photographer's visual axis and fixation point in the present embodiment are executed by the software of the microcomputer of the visual axis calculation processing apparatus on the basis of the aforementioned express ions.

The coefficients for correcting the individual difference of the visual axis are found, the position, on the focusing screen, of the visual axis of the observer looking into the finder of the camera is calculated by the use of expression (5), and the visual axis information is utilized for the focus adjustment of the photo-taking lens or for exposure control or the like.

As described above, the direction coordinates of the photographer's visual axis can be calculated from the positional relation between the corneal reflected image ("Purkinje's image", hereinafter referred to as "P-image") of the infrared light emitting diode for illumination (hereinafter referred to as "IRED") and the pupil in the eyeball image. A specific detection system for this is disclosed in U.S. patent appln. Ser. No. 07/888,495 (filed on May 27, 1992).

Since the P-image is the corneal reflected image of the IRED, its luminance is high in the whole of the eyeball image, and since that image is also the reflected image of the chip light emitting surface of the IRED, its size is very small. Accordingly, if those characteristics are utilized, the P-image can be extracted from the eyeball image signal. Specifically, where the luminance value of a certain pixel in the eyeball image signal exceeds a predetermined value and the luminance difference between that pixel and the pixels around it exceeds a predetermined level, that pixel (or the surrounding pixel area including that pixel) is chosen as the candidate for the P-image.

Further, design is made such that one set of two IREDs is turned on to detect the distance between the camera and the eyeball and the P-image is used in a pair and therefore, when there are a plurality of objects for the pair of P-images, a pair of P-images having an appropriate spacing therebetween is selected.

When as shown in FIGS. 1A and 1B, there are one set of high luminance portions (52a and 52b), it can be readily detected with the aforedescribed condition that these high luminance portions are right P-images.

However, when as shown in FIG. 2, there are a plurality of sets of high luminance portions, it will often be the case with the aforedescribed condition alone that the P-images are erroneously selected, and this is very inconvenient for visual axis detection.

SUMMARY OF THE INVENTION

The present invention intends to solve the above-noted problem.

That is, when the result of the visual axis calculated on the basis of a pair of P-images selected at first is apparently not normal, if as shown in FIG. 2, there is further a pair of P-images which are candidates, the present invention intends to try the calculation of the visual axis by the use of a discrete pair of P-images to thereby make the selection of a right P-image possible.

A preferred embodiment of the present invention is provided with means for illuminating an observer's eyeball, first means for detecting the characteristic portion of the image of the observer's eyeball, second means for detecting the corneal reflected image by said illuminating means for the image of the observer's eyeball, means for selecting some corneal reflected image from among the corneal reflected images obtained by said second detecting means, visual axis detecting means for detecting the observer's visual axis from the positional relation between said characteristic portion and said selected corneal reflected image, means for evaluating the state of the detected visual axis, and means for reselecting a discrete corneal reflected image when the state of the visual axis is evaluated as being inappropriate by said evaluating means,

BRIEF DESCRIPTION OF THE DRAWINGS

FIG. 7 is a flow chart of the visual axis detection according to the present invention.

FIG. 12 is another flow chart of visual axis detection according to the present invention.

DETAILED DESCRIPTION OF THE PREFERRED EMBODIMENTS

Figure 3:
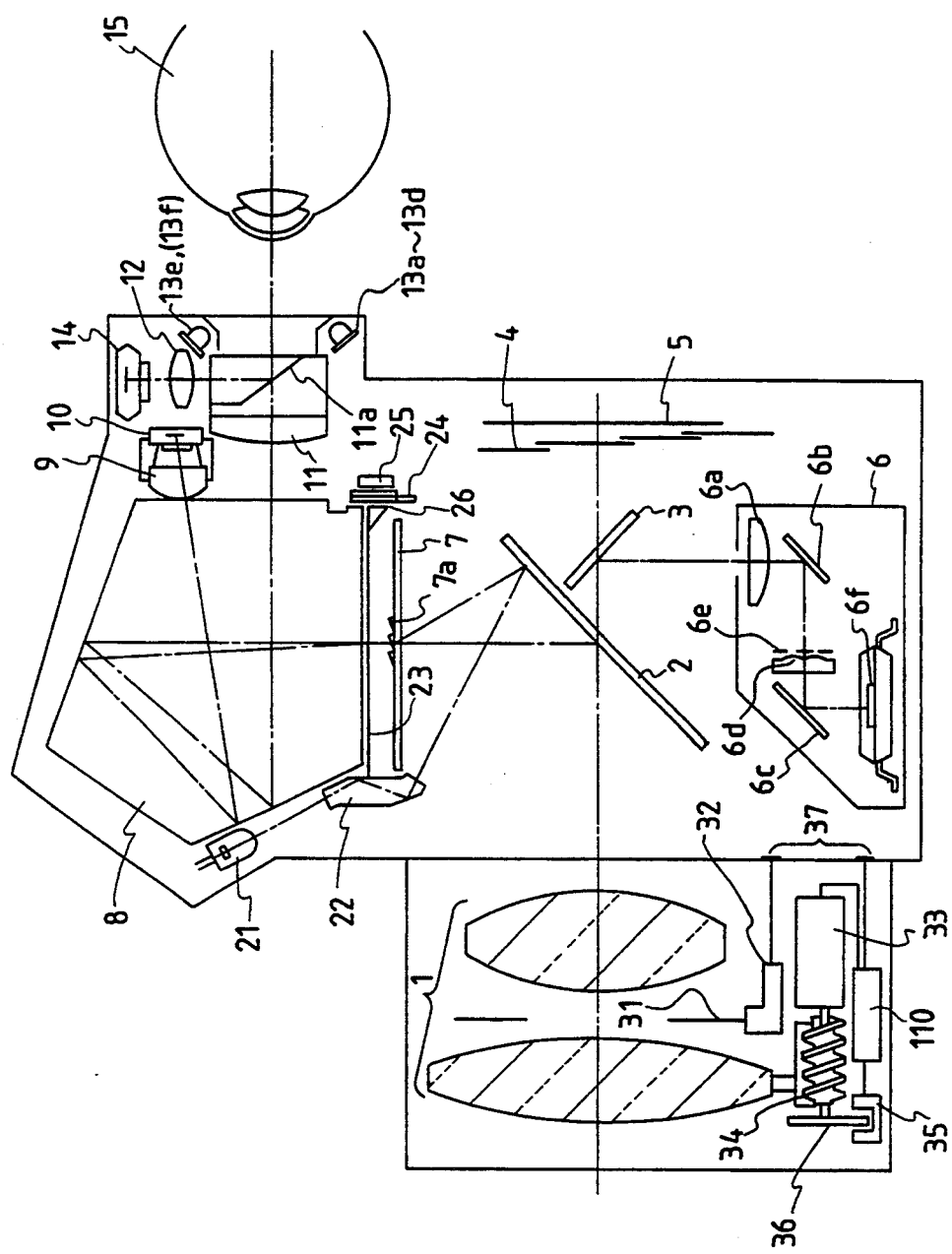
FIG. 3 is a schematic view of the essential portions of Embodiment 1 in which the present invention is applied to a single-lens reflex camera.

FIG. 3 is a schematic view of the essential portions of Embodiment 1 when the present invention is applied to a single-lens reflex camera.

In this figure, the numeral 1 designates a photo-taking lens which, for the sake of convenience, is shown as being comprised of two lenses, but actually it is comprised of a greater number of lenses. The numeral 2 denotes a main mirror adapted to obliquely contact with or be retracted to a photographing optical path in conformity with the observed state of the object image by a finder system and the photographed state of the object image. The numeral 3 designates a sub-mirror for reflecting a light beam transmitted through the main mirror 2 toward a focus detecting device 6 in a camera body which will be described later.

The numeral 4 denotes a shutter, and the numeral 5 designates a photosensitive member comprising silver salt film or an image pickup tube such as a CCD or MOS type image pickup element or a vidicon.

The focus detecting device 6 is comprised of a field lens 6a disposed near the imaging plane, reflecting mirrors 6b and 6c, a secondary imaging lense 6d, a stop 6e, a line sensor 6f comprising a plurality of CCDs, etc.

Figure 4:
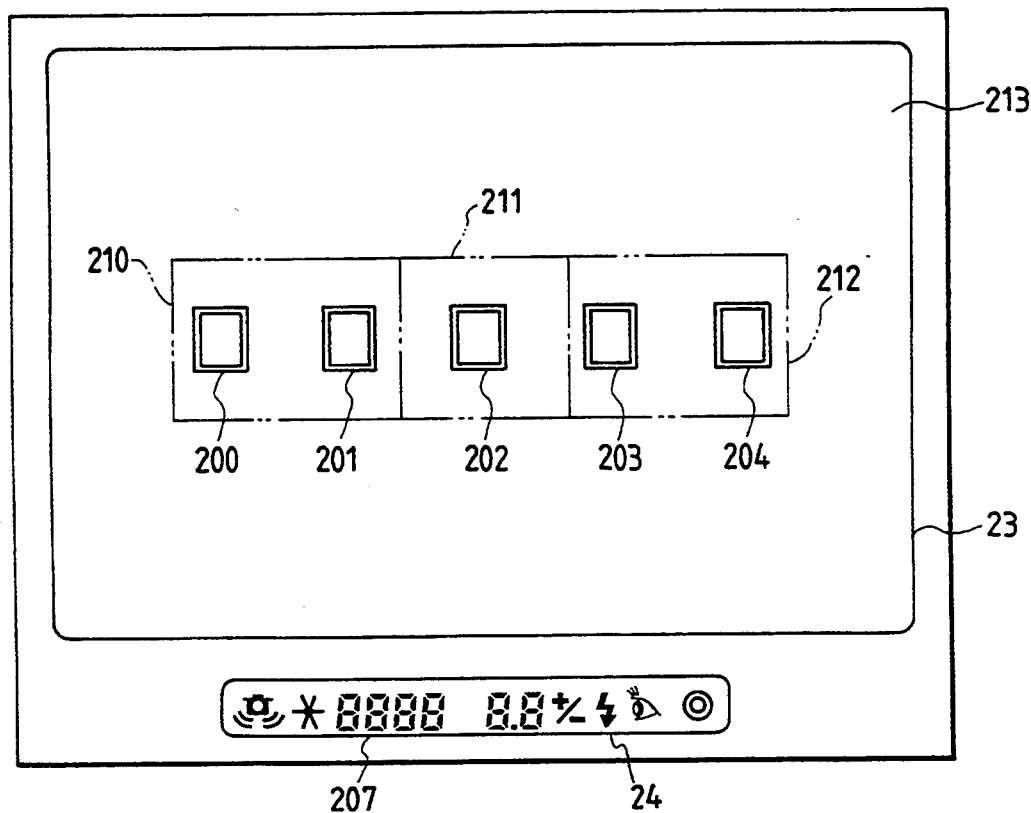
FIG. 4 is an illustration of the finder field of FIG. 3.

The focus detecting device 6 in the present embodiment adopts a well-known phase difference system, and is designed such that as shown in FIG. 4, with a plurality of (five) areas in the observation image field (in the finder field) as distance measuring points, these distance measuring points become capable of detecting the focus.

The numeral 7 denotes a focusing screen disposed on the predetermined imaging plane of the photo-taking lens 1, the numeral 8 designates a pentagonal prism for changing the finder optical path, and the numerals 9 and 10 denote an imaging lens and a photometry sensor, respectively, for measuring the object luminance in the observation image field. The imaging lens 9 relates the focusing screen 7 and the photometry sensor 10 conjugately with each other through a reflecting optical path in the pentagonal prism 8.

An eyepiece 11 provided with a light divider 11a is disposed rearwardly of the exit surface of the pentagonal prism 8 and is used for the observation of the focusing screen 7 by a photographer's eye 15. The light divider 11a comprises, for example, a dichroic mirror transmitting visible light therethrough and reflecting infrared light.

The numeral 12 designates a light receiving lens, and the numeral 14 denotes an image sensor comprising an array of two-dimensionally arranged photoelectric elements such as CCDs. The image sensor 14 is disposed so as to be conjugate with the vicinity of the pupil of the photographer's eye 15 located at a predetermined position with respect to the light receiving lens 12. The numerals 13a-13f designate infrared light emitting diodes which are illuminating light sources.

The numeral 21 denotes an LED of high luminance for superimposition which can be visually recognized even in a bright object. Light emitted from this LED 21 passes through a prism 22 for light projection, is reflected by the main mirror 2, is bent in a vertical direction by a minute prism array 7a provided on the indicating portion of the focusing screen 7, and passes through the pentagonal prism 8 and the eyepiece 11 to the photographer's eye 15.

So, the minute prism array 7a is formed into a frame-like shape at a plurality of locations (distance measuring points) corresponding to the focus detection areas of the focusing screen 7, and is illuminated by five LEDs 21 for superimposition (respective ones of which are referred to as LED-L1, LED-L2, LED-C, LED-R1 and LED-R2) corresponding to the plurality of distance measuring points.

Thereby, as can be seen from the finder field shown in FIG. 3, distance measuring point marks 200, 201, 202, 203 and 204 shine in the finder field, whereby the focus detection areas (distance measuring points) can be indicated (this will hereinafter be referred to as the superimpose indication).

The numeral 23 designates a field mask forming the finder field area, and the numeral 24 denotes an LCD in the finder for indicating photographing information outside the finder field. The LCD 24 is illuminated by an illuminating LED (F-LED) 25.

Light transmitted through the LCD 24 is directed into the finder field by a triangular prism 26, and is indicated outside the finder field as shown at 207 in FIG. 4 and thus, the photographer can know the photographing information.

The numeral 31 designates a stop provided in the photo-taking lens 1, the numeral 32 denotes an aperture driving device including an aperture drive circuit 111 which will be described later, the numeral 33 designates a lens driving motor, the numeral 34 denotes a lens driving member comprising a driving gear, etc., and the numeral 35 designates a photocoupler which detects the rotation of a pulse plate 36 operatively associated with the lens driving member 34 and transmits it to a focus adjusting circuit 110. The focus adjusting circuit 110 is designed to drive the lens driving motor by a predetermined amount on the basis of this information and the information of the amount of lens driving from the camera side to thereby move the photo-taking lens 1 to the in-focus position. The numeral 37 denotes a mount contact which provides a conventional interface between the camera and the lens.

Figure 5:
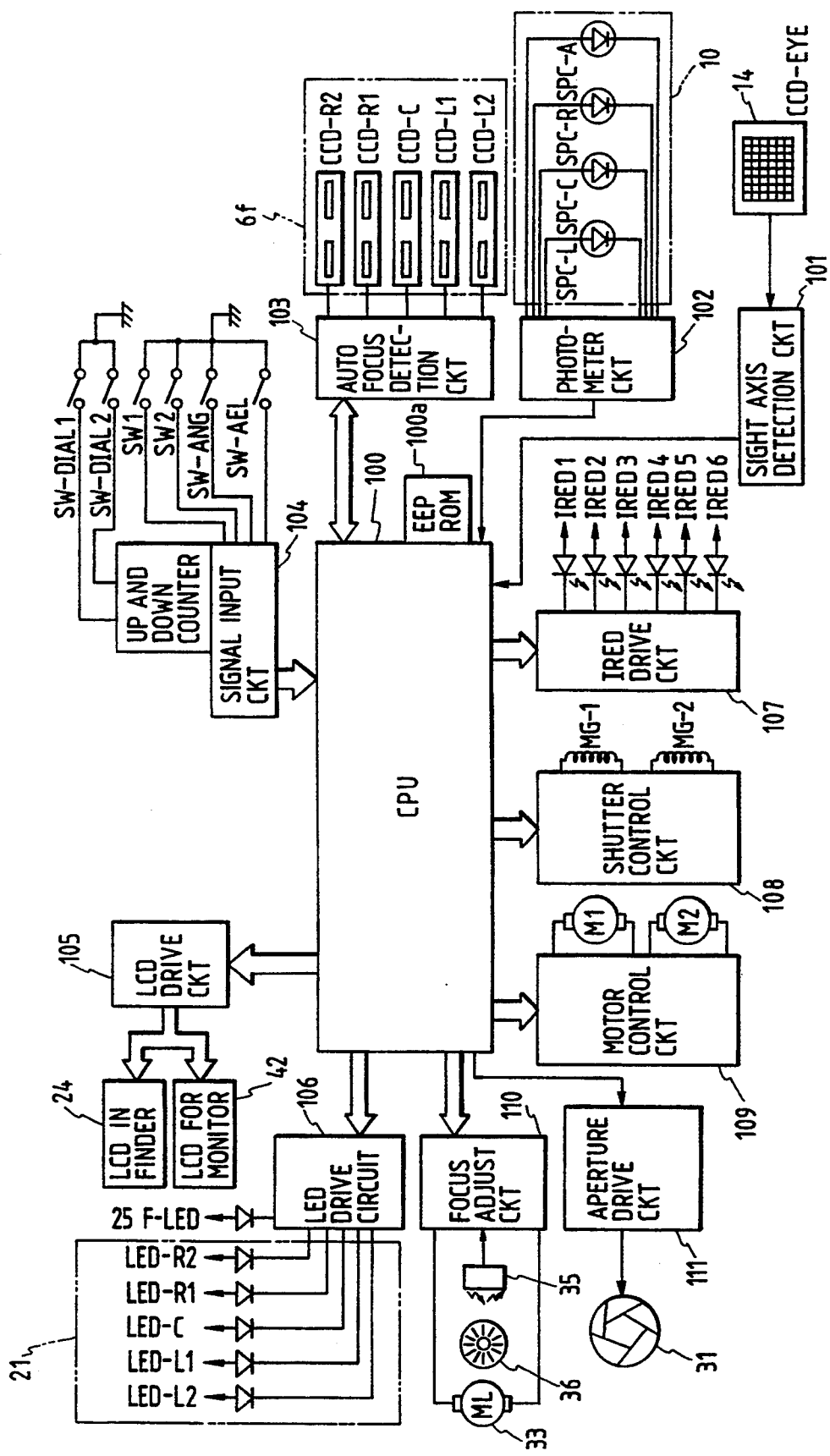
FIG. 5 is a diagram of the electric circuit of an optical apparatus according to the present invention.

FIG. 5 is a diagrammatic illustration of electric circuits contained in the camera of the present invention. In FIG. 5, the same portions as those in FIG. 3 are given the same numerals.

A sight axis detection circuit 101, a photometer circuit 102, an auto focus detection circuit 103, a signal input circuit 104, an LCD drive circuit 105, an LED drive circuit 106, an IRED drive circuit 107, a shutter control circuit 108 and a motor control circuit 109 are connected to the central processing unit (hereinafter referred to as the CPU) 100 of a microcomputer contained in the camera body. Also, the transmission of a signal to the focus adjusting circuit 110 and aperture drive circuit 111 disposed in the photo-taking lens is effected through the mount contact 37 shown in FIG. 3.

EEPROM 100a incident to the CPU 100 is memory means having the function of memorizing visual axis correction data for correcting the individual difference of visual axis.

The sight axis detection circuit 101 A/D-converts the output of the eyeball image from the image sensor 14 (CCD-EYE), and transmits this image information to the CPU 100. The CPU 100, as will be described later, extracts the characteristic points of the eyeball image necessary for visual axis detection in accordance with a predetermined algorithm and further, calculates the photographer's visual axis from the position of each characteristic points.

The photometer circuit 102 amplifies the output from the photometry sensor 10, and thereafter logarithmically compresses and A/D-converts it, which is then sent as the luminance information of each sensor to the CPU 100. The photometry sensor 10 is comprised of a photodiode for photometering four areas, i.e., SPC-L for photometering a left area 210 including left distance measuring points 200 and 201 in the finder field shown in FIG. 4, SPC-C for photometering the central area 211 including the central distance measuring point 202, SPC-R for photometering a right area 212 including right distance measuring points 203 and 204, and SPC-A for photometering the area 213 around these.

The line sensor 6f of FIG. 5 is a conventional CCD line sensor comprised of five sets of line sensors CCD-L2, CCD-L1, CCD-C, CCD-R1 and CCD-R2 corresponding to five distance measuring points 200–204 in the image field, as shown in FIG. 4.

The auto focus detection circuit 103 A/D-converts a voltage obtained from the line sensor 6f and sends it to the CPU 100. SW-1 designates a switch adapted to be closed by the first stroke of a release button 41 and start photometering, AF and visual axis detecting operations, SW-2 denotes a release switch adapted to be closed by the second stroke of the release button, SW-AEF designates an AE lock switch adapted to be closed by an AE lock button 43 being depressed, and SW-DIAL1 and SW-DIAL2 denote dial switches provided in an electronic dial, not shown. These dial switches count the amount of rotation click of the electronic dial input to the up and down counter of the signal input circuit 104.

The numeral 105 designates a conventional LCD drive circuit for display-driving a liquid crystal display element LCD. This LCD drive circuit 105 can cause an LCD 42 for monitor and an LCD 24 in the finder to display an aperture value, a shutter time, a set photographing mode, etc. at a time in accordance with a signal from the CPU 100. The LED drive circuit 106 ON-OFF-controls an LED for illumination (F-LED) 25 and an LED for superimpose 21. The IRED drive circuit 107 selectively turns on infrared light emitting diodes (IRED1-6) 13a–13f in conformity with the situation.

The shutter control circuit 108 controls a magnet MG-1 which, when electrically energized, moves a front curtain and a magnet MG-2 which, when electrically energized, moves a rear curtain, and exposes the photosensitive member to a predetermined quantity of light. The control circuit 169 is for controlling a motor M1 for effecting the winding and rewinding of film and the main mirror 2 and a motor M2 for effecting the charging of the shutter 4. A series of release sequences of the camera are operated by the shutter control circuit 108 and motor control circuit 109.

Figure 6B:
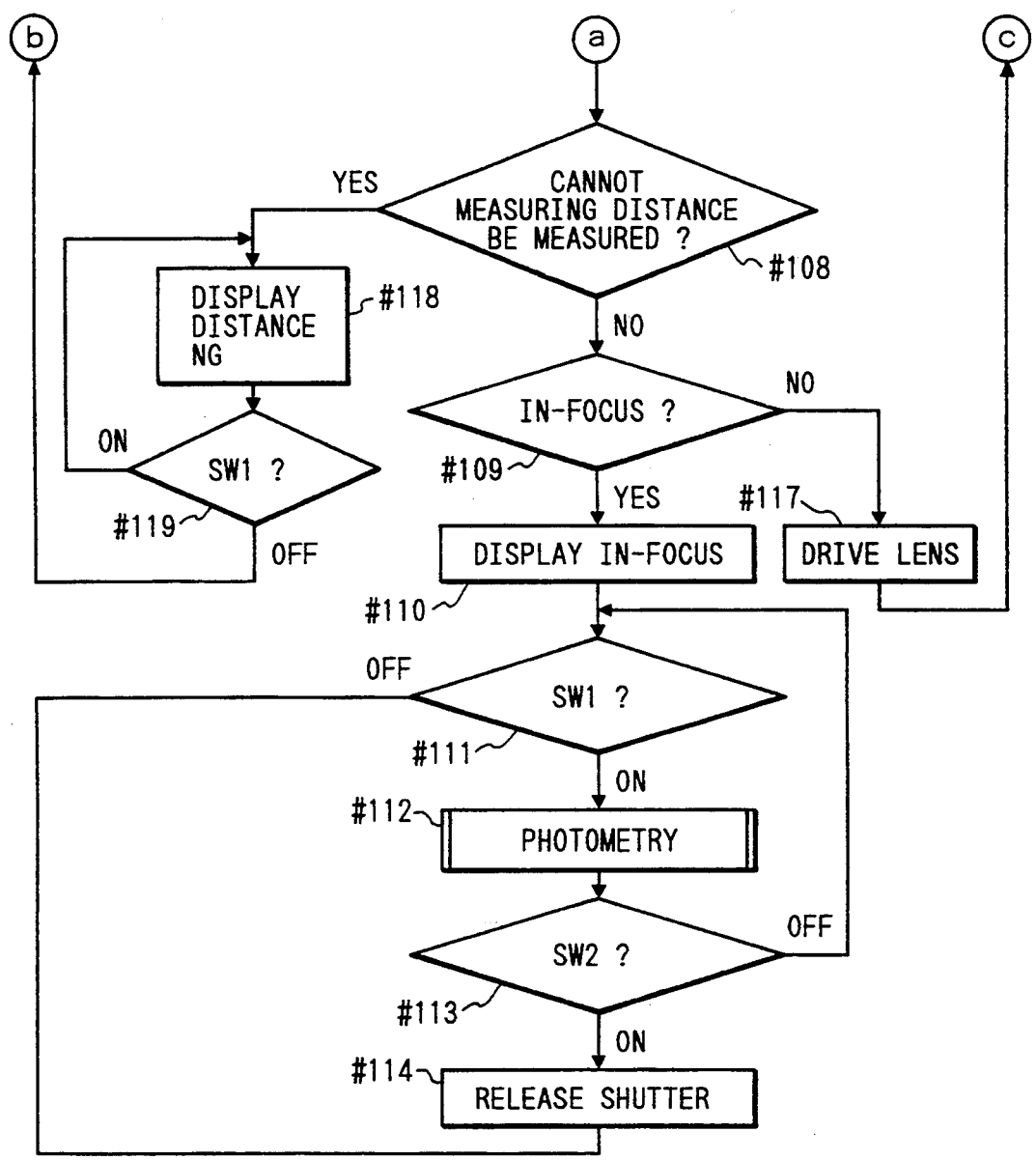
FIG. 6 is comprised of FIGS. 6A and 6B showing flow charts of the operation of the optical apparatus of FIG. 5.

A flow chart of the operation of the camera having the visual axis detecting device is shown in FIGS. 6A and 6B, and description will hereinafter be made with reference to this flow chart.

When a mode dial, not shown, is turned to set the camera from its inoperative state to a predetermined photographing mode (in the present embodiment, description will be made on the basis of a case where the camera has been set to the shutter priority AE), and power source switch of the camera is closed (#100), and variables used for the visual axis detection by the CPU 100 are reset.

The camera waits until the release button 41 is depressed and the switch SW1 is closed (#102). When the signal input circuit 104 detects that the release button 41 has been depressed and the switch SW1 has been closed, the CPU 100 confirms it to the sight axis detection circuit 101 (#103).

If at this time, the camera is set to the sight axis prohibition mode, a particular distance measuring point is selected by a distance measuring point auto selection subroutine (#116) without sight axis detection being executed, i.e., without sight axis information being used. At this distance measuring point, the auto focus detection circuit 103 performs the focus detecting operation (#107).

As described above, the camera is provided with both of a photographing mode for effecting distance measuring point selection without using the sight axis information (the sight axis prohibition auto focus photographing mode) and a photographing mode for effecting distance measuring point selection by the use of the sight axis information (the sight axis auto focus photographing mode), and is designed such that the photographer can arbitrarily select one of these modes depending on whether the camera is set to the sight axis prohibition mode.

Several methods would occur to mind as the algorithm of distance measuring point auto selection, but the near point priority algorithm which places weighting on the central distance measuring point is effective, and this has nothing direct to do with the present invention and therefore need not be described.

When the camera is set to the visual axis detection mode, visual axis detection is executed (#104). At this time, the LED drive circuit 106 turns on the illuminating LED (F-LED) 25, the LCD drive circuit 105 turns on the visual axis input mark 78 of the LCD 24 in the finder, and the photographer can confirm in the outside 207 of the finder screen that the camera is performing visual axis detection.

The sight axis detected in the sight axis detection circuit 101 is converted into target point coordinates on the focusing screen 7. The CPU 100 selects a distance measuring point proximate to the target point coordinates, transmits a signal to the LED drive circuit 106 and turns on and off the distance measuring point mark by the use of the LED 21 for superimposition (#105).

When the photographer sees the distance measuring point selected by the photographer's visual axis be displayed and recognizes that distance measuring point is not correct, and releases the release button 41 to open the switch SW1 (#106), the camera waits until the switch SW1 is closed (#102).

As described above, design is made such that the photographer is informed by the distance measuring point mark in the finder field being turned on and off that the distance measuring point has been selected by the visual axis information and therefore, the photographer can confirm whether the distance measuring point has been selected as he intends.

If the photographer, seeing the distance measuring point selected by the visual axis be displayed, continues to close the switch SW1 (#106), the auto focus detection circuit 103 executes the focal point detection of one or more distance measuring points by the use of the detect visual axis information (#107).

Whether the selected distance measuring point cannot be measured is judged (#108), and if it cannot be measured, the CPU 100 sends a signal to the LCD drive circuit 105 to thereby turn on and off the in-focus mark of the LCD 24 in the finder, and warns the photographer that distance measurement is NG (impossible) (#118), and continues this state until the switch SW1 is released (#119).

If distance measurement is possible and the focus adjusted state of the distance measuring point selected by a predetermined algorithm is not in-focus (#109), the CPU 100 sends a signal to the lens focus adjust circuit 110 to thereby drive the photo-taking lens 1 by a predetermined amount (#117). After the driving of the lens, the auto focus detection circuit 103 again effects focal point detection (#107) and judges whether the photo-taking lens 1 is in focus (#109).

If at a predetermined distance measuring point, the photo-taking lens 1 is in focus, the CPU 100 sends a signal to the LCD drive circuit 105 to thereby turn on the in-focus mark of the LCD 24 in the finder and also sends a signal to the LED drive circuit 106 to thereby make the in-focus distance measuring point 201 display in-focus (#110).

It is often the case that at this time, the display of the distance measuring point selected by the visual axis is turned off, but the distance measuring point in-focus displayed and the distance measuring point selected by the visual axis coincide with each other and therefore, the in-focus distance measuring point is set to a turned-on state to make the photographer recognize the in-focus. When seeing the in-focus distance measuring point be displayed in the finder, the photographer recognizes that distance measuring point is not correct and releases the release button 41 to thereby open the switch SW1 (#111), the camera continues to wait until the switch SW1 is closed (#102).

Also, if seeing the in-focus-displayed distance measuring point, the photographer continues to close the switch SW1 (#111), the CPU 100 sends a signal to the photometer circuit 102 to thereby effect photometry (#112). At this time, an exposure value with weighting effected on the photometer areas 210–213 including the in-focus distance measuring point is calculated.

The release button 41 is further depressed and whether the switch SW2 is closed is judged (#113), and if the switch SW2 is in its OFF state, the state of the switch SW1 is confirmed again (#111). If the switch SW2 is closed, the CPU 100 sends signals to the shutter control circuit 108, the motor control circuit 109 and the aperture drive circuit 111, respectively.

The motor M2 is first electrically energized to move the main mirror 2 up and stop down the aperture 31, whereafter the magnet MG1 is electrically energized to open the front curtain of the shutter 4. The aperture value of the aperture 31 and the shutter speed of the shutter 4 are determined by the exposure value detected by the photometer circuit 102 and the speed of the film 5. After the lapse of a predetermined shutter time (e.g. 1/250 sec.), the magnet MG2 is electrically energized to close the rear curtain of the shutter 4. When the exposure of the film 5 is completed, the magnet MG2 is again electrically energized to effect mirror down and shutter charge, and the motor M1 is also electrically energized to effect the frame feeding of the film, and the operation of a series of shutter release sequences is completed (#114). Thereafter, the camera waits until the switch SW1 is closed again (#102).

Figure 8:
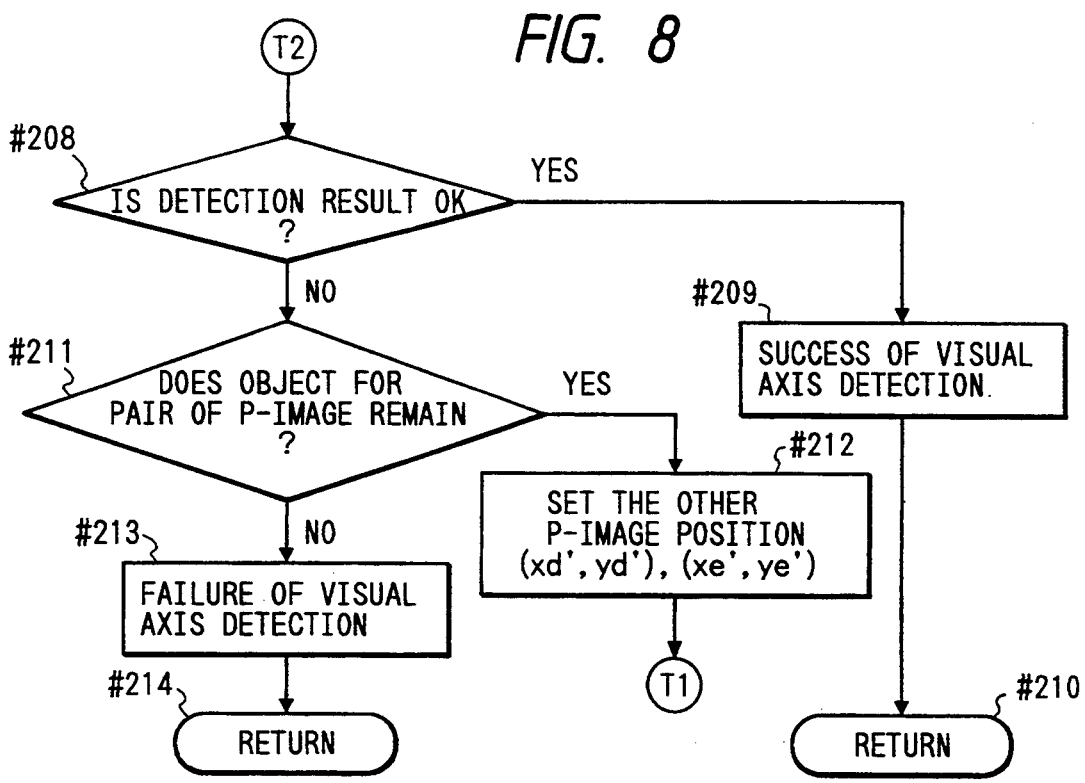
FIG. 8 is a flow chart of the visual axis detection according to the present invention (a first embodiment)

FIGS. 7 and 8 are flow charts of the visual axis detection of the present invention.

As previously described, when it receives a signal from the CPU 100, the sight axis detection circuit 101 executes visual axis detection (#104).

First, the CPU 100 selects an IRED of an appropriate combination from among the infrared light emitting diodes (IREDs) 13a–13f for illuminating the photographer's eye and turns on that IRED (#201). The selection of the IRED is done by a posture switch, not shown, depending on whether the camera is in its horizontal position or its vertical position, or whether the photographer wears spectacles.

Subsequently, the image sensor 14 effects charge accumulation for a predetermined accomulation time (#202). When the charge accumulation is completed, the IRED is turned off (#203).

The CPU 100 reads out the photographer's eyeball image from the image sensor 14 which has completed the charge accumulation and at the same time, sequentially effects the extraction of the characteristics of the P-image and the pupil portion (#204). A specific method for this is described in detail in U.S. application Ser. No. 07/888,495 and therefore need not be described in detail herein.

Figure 1A:
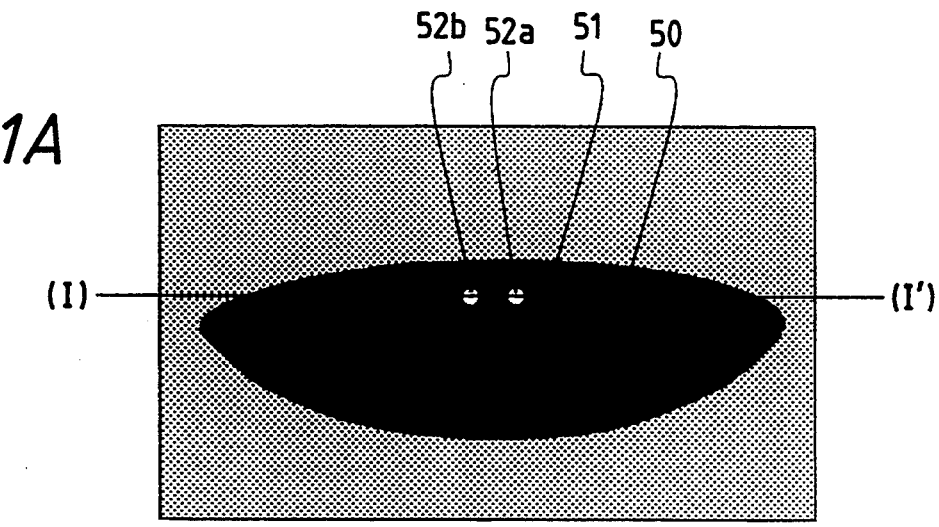
FIGS. 1A and 1B show the image of a very normal photographer's eyeball.
Figure 1B:
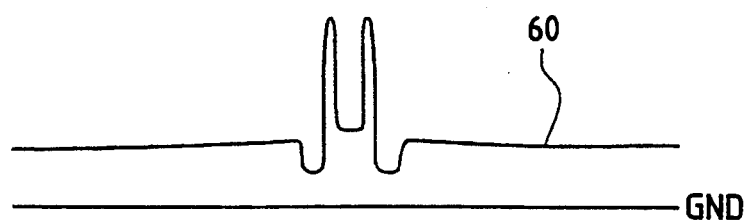
Figure 2:
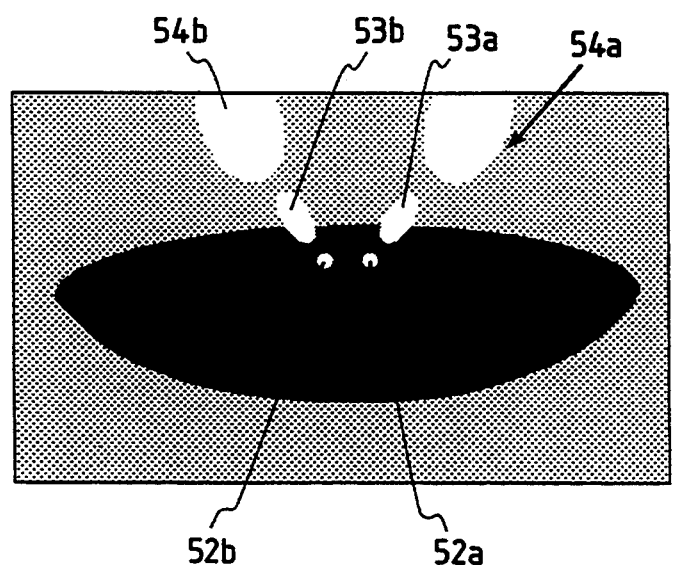
FIG. 2 shows the image of the eyeball of a photographer wearing spectacles.

Now, after the reading-out of the whole eyeball image is completed and the extraction of the characteristics of a plurality of P-images and the pupil is completed, the positions of one set of P-images are detected on the basis of this information (#205). As previously described, the P-image is the corneal reflected image of the eyeball illuminating IRED and therefore appears as a calescence point of high intensity of light in the image signal and thus, one set of P-images can be detected with that characteristic and the position $(xd', yd')$ and $(xe', ye')$ thereof can be found. In the case of the eyeball image is shown in FIGS. 1A and 1B, there is only one set of calelscence points like P-images and therefore, the detection thereof is easy, but when as shown in FIG. 2, there is created a ghost attributable to the spectacles the photographer wears, detecting a pair of correct P-images often results in failure. To recognize P-images, it is desirable to add, in addition to the calescence point condition, the spacing between the P-images forming a pair, or the size of the calescence point on the sensor to the conditions. This is because generally in the ghost by spectacles, a calescence point exists greatly.

If at any rate, one pair of P-images can be determined at (#205), the detection of the center of the pupil $(xe', ye')$ and the diameter $(vc)$ of the pupil is subsequently effected (#206).

If the positions of the P-images and the pupil can be detected from the photographer's eyeball image, the direction of the photographer's visual axis or the coordinates on the finder can be calculated from expression (5) (#207).

In FIG. 8, subsequently, the CPU 100 judges, whether the result of the detected visual axis can be used (#208). Specifically, it judges whether the rotation angle of the detected eyeball is abnormally great in both the horizontal and the vertical direction. This is because as long as the photographer normally looks into the finder, the rotation angle ought not to be too great, and it is considered that if the calculated rotation angle exceeds a predetermined angle (e.g. the order of 20°), the P-images have been erroneously detected. This criterion of judgment may be not only the rotation angle, but also whether the target point is within or outside the field coordinates.

If the result of the detection is OK, it is regarded as the "success of visual axis detection" (#209) and the routine of visual axis detection is returned (#210).

If the result of the detection is not normal, it is regarded as there being the possibility that a pair of P-images have been erroneously selected, and whether there is another pair of P-images is examined (#211). In the case of the eyeball image as shown in FIG. 2, there are three pairs of P-images (52a, 52b), (53a, 53b) and (54a, 54b). Of course, the pair of P-images (52a, 52b) is correct and the pairs (53a, 53b) and (54a, 54b) are the ghosts by the spectacles. When the pair of P-images (52a, 52b) is selected from first, the result of the detection is correct, but when the pair (53a, 53b) is selected at first and visual axis detection is effected, the result of the detection will become abnormal. So, if as in the example shown in FIG. 2, there are a plurality of objects for a pair of P-images, another pair of P-images is selected (#212) and visual axis detection is tried again (T1).

When as shown in FIGS. 1A and 1B, there are only one pair of P-images, even if that pair is an uncorrect pair of P-images, it is impossible to reselect another pair and therefore, in that case, it is regarded as the "failure of visual axis detection" (#213) and the routine of visual axis detection is returned (#214).

In the embodiment hitherto described, if the result of the visual axis calculated on the basis of the pair of P-images selected at first is normal, the process is terminated there, and if not so, another pair of P-images is re-selected and at a point of time whereat the result has become normal, the process of visual axis detection is terminated.

However, when there is a plurality of objects for a pair of P-images, particularly when the ghost by spectacles exists very near a true P-image, if visual axis calculation is effected with that ghost as a P-image, a fair result will be presented and it may happen that the process ends with it.

So, in a second embodiment of the present invention, there is proposed a processing method whereby the calculation of visual axis is generally executed with all objects for a pair of P-images and the most probable result is adopted from the result of the calculation.

Figure 9:
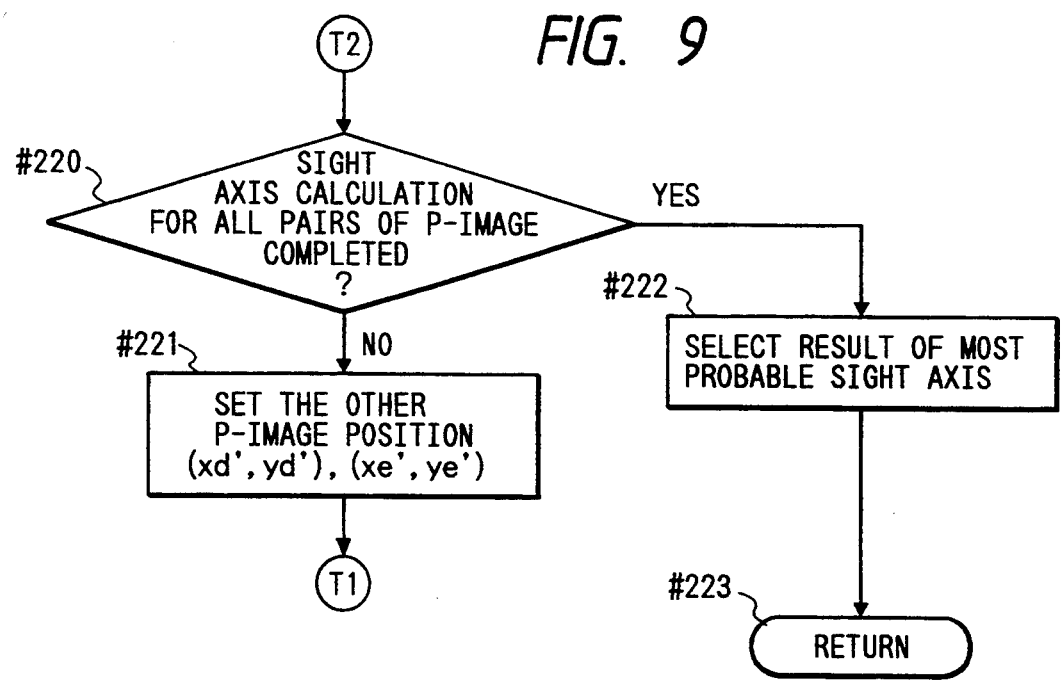
FIG. 9 is a flow chart of the visual axis detection according to the present invention (a second embodiment).
Figure 10:
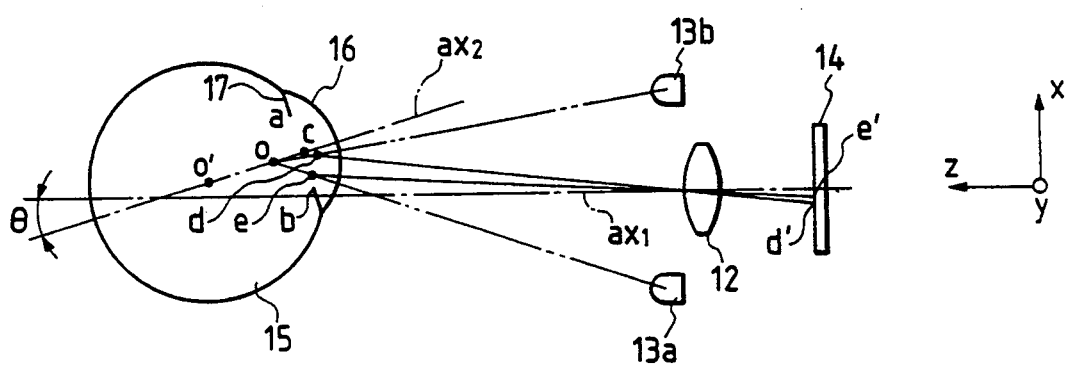
FIG. 10 illustrates a visual axis detecting method according to the prior art.

FIG. 9 shows a flow chart of the second embodiment.

When the calculation of visual axis is terminated at the step #207 of FIG. 7, shift is made to a step #220, where whether sight axis calculation has been completed for all objects for pairs of P-images is judged. In the example of the eyeball image as shown in FIGS. 1A and 1B, there is only one pair of P-images and therefore, one calculation is enough and the result thereof is used as the final result (#222), and the routine of sight axis calculation is returned (#223).

In the example of the eyeball image as shown in FIG. 2, there are three pairs of P-images (actually the high luminance area of large expanse should be excluded as ghost at first and should not be included among objects for pairs of P-images, but here it is to be understood for description that in the example of the eyeball image shown in FIG. 2, there are objects for three pairs of P-images) and therefore, even if the result of sight axis detection by the pair of P-images selected at first is good at all, another pair of P-images is re-set (#221) and the calculation of sight axis is effected again.

When the calculations by three pairs of P-images are terminated, the most probable sight axis result is adopted from among the results of those calculations (#222).

Specifically, a method of adopting the result of the smallest one of the detected rotation angles the eyeball by the pairs of P-images is realistic. If the final result of the sight axis is adopted, the sight axis detection routine is returned (#223).

As described above, according to the present invention, when the result of the detection of the sight axis calculated on the basis of a selected pair of P-images is apparently not normal, if there are objects for another pair of P-images, the calculation of the sight axis is effected again on the basis of that pair of P-image, whereby a good sight axis detecting operation can be made possible even in the case of a photographer wearing spectacles.

Still another embodiment of the present invention will now be described with reference to FIG. 11.

In the present embodiment, whether the visual axis detection at this time has been effected rightly is judged on the basis of the distance information L from the predetermined position of the apparatus to the eyeball. A specific method of finding the distance is carried out in the following manner.

By the use of the spacing $\Delta p = |xd' - xe'|$ between the positions $xd'$ and $xe'$ of two P-images on the image sensor 14, the distance L is found, for example, from an equation $$L = \frac{a_1}{\Delta P} + a_2.$$

As an example, supposing an optical system in which the spacing A p on the image sensor 14 is of the order of 8 pixels when the distance L between the camera and the observer's eyeball is 25 mm, by setting $a_1$ and $a_2$ to the order $-165$ and the order of 3.8, respectively, the distance L can be calculated if $\Delta p$ is found. When the calculated distance L is e.g. 5 mm or less or 40 mm or greater, a situation like that is an impossible one and therefore, it is judged that the visual axis detection at such time is unusable.

That is, the visual axis information is invalidated. The CPU 100 has the function as invalidating means for invalidating the visual axis information like this. If the result of the detection is OK, it is regarded as the "success of visual axis detection" (#309), and the routine of visual axis detection is returned (#310).

On the other hand, if the result of the detection is not normal, it is regarded as there being the possibility of the pair of P-images having been erroneously selected, and whether there is another pair of P-images is examined (#311).

In the case of the eyeball image as shown in FIG. 2, there are three sets of reflected images (52a, 52b) (53a, 53b) and (54a, 54b) as pairs of P-images. Of course, (52a, 52b) is the right pair of P-images, and the pairs of reflected images (53a, 53b) and (54a, 54b) are the ghost by the spectacles.

When the pair of P-images (52a, 52b) is selected from first, a correct result of detection is given, but when the pair of reflected images (53a, 53b) is selected at first and visual axis detection is effected, the result of the detection becomes not normal.

So, if as in the example shown in FIG. 2, there is a plurality of objects for the pair of P-images, another pair of P-images is selected (#312) and visual axis detection is tried again (T1).

When as shown in FIG. 8, there is only one pair of P-images from first, even if that pair is an incorrect pair of P-images, it will be impossible to reselect another pair of P-images and therefore, in that case, it is regarded as the "failure of visual axis detection" (#313) and the routine of visual axis detection is returned (#314). In the present embodiment a correct pair of P-images is selected in the manner described above, whereby the information of the photographer's visual axis is obtained highly accurately.

In the above-described embodiments, by detecting whether the visual angle is within or outside a predetermined range or whether the distance between eyeballs is within or outside a predetermined range, the determination of the visual axis is done, but by combining the measurement of the visual angle and the measurement of the distance between eyeballs as in the flown shown in FIG. 12 (#208 and #208-1), it becomes possible to determine the visual axis more finely and more accurately.

What is claimed is:

1. A visual axis detecting apparatus comprising:
   means for illuminating an observer's eyeball;
   first means for detecting the characteristic portion of the image of the observer's eyeball;
   second means for detecting the corneal reflected image by said illuminating means from the image of the observer's eyeball;
   means for selecting some corneal reflected image from among the corneal reflected images obtained by said second detecting means;
   visual axis detecting means for detecting the observer's visual axis from the positional relation between said characteristic portion and said selected corneal reflected image;
   means for evaluating the state of the detected visual axis; and
   means for reselecting another corneal reflected image when it is evaluated by said evaluating means that the state of the visual axis is inappropriate.

2. A visual axis detecting apparatus according to claim 1, wherein said characteristic portion includes a pupil.

3. A visual axis detecting apparatus according to claim 1, wherein said first means includes a CPU.

4. A visual axis detecting apparatus according to claim 1, wherein said second means includes a CPU.

5. A visual axis detecting apparatus according to claim 1, wherein said evaluating means includes a CPU.

6. A visual axis detecting apparatus according to claim 1, wherein said evaluating means judges whether the rotation angle of the visual axis is greater than that of a predetermined level.

7. A visual axis detecting apparatus according to claim 1, wherein said evaluating means judges whether the visual axis is within or outside field coordinates.

8. A visual axis detecting apparatus comprising:
   means for illuminating an observer's eyeball;
   first means for detecting the characteristic portion of the image of the observer's eyeball;
   second means for detecting a corneal relfected image from the image of the observer's eyeball;
   means for selecting some corneal reflected image from among a plurality of corneal reflected images obtained by said second means;
   visual axis detecting means for detecting the observer's visual axis from the positional relation between said characteristic portion and said selected corneal reflected image, said visual axis detecting means being also effective to detect the visual axis from another corneal reflected image and said characteristic portion; and
   determination means for determining a visual axis from a plurality of visual axes detected by said visual axis detecting means.

9. A visual axis detecting apparatus according to claim 8, wherein said characteristic portion includes a pupil.

10. A visual axis detecting apparatus according to claim 8, wherein said first means includes a CPU.

11. A visual axis detecting apparatus according to claim 8, wherein said second means includes a CPU.

12. A visual axis detecting apparatus according to claim 8, wherein said determining means determines a visual axis of which the rotation angle is the smallest.

13. A visual axis detecting apparatus comprising:
    illuminating means for illuminating an observers' eyeball;
    light receiving means having a plurality of sensor elements and receiving light reflected from the eyeball;
    evaluating means for evaluating the state of visual axis on the basis of the positional information of a sensor element exhibiting a relatively high output; and
    means for extracting the position of another sensor element exhibiting a relatively high output when the state of visual axis is evaluated to be inappreciative by said evaluating means.

14. A visual axis detecting apparatus according to claim 13, wherein said illuminating means has a plurality of light emitting sources.

15. A visual axis detecting apparatus according to claim 13, wherein said evaluating means evaluates whether the angle of visual axis is within or above a predetermined angle.

16. A visual axis detecting apparatus according to claim 13, wherein said evaluating means measures the distance between the positions of at least two sensor elements exhibiting high outputs, and when said distance is outside a predetermined range, said extracting means extracts the position of another sensor element exhibiting a high output.

17. A visual axis detecting apparatus according to claim 13, wherein said evaluating means further evaluates the state of visual axis on the basis of the positional information of a sensor element exhibiting a relatively low output.

* * * * *

UNITED STATES PATENT AND TRADEMARK OFFICE
CERTIFICATE OF CORRECTION

PATENT NO. : 5,402,199
DATED : March 28, 1995
INVENTOR(S) : AKASHI, A.

Page 1 of 2

It is certified that error appears in the above-indentified patent and that said Letters Patent is hereby corrected as shown below:

On the title page, item [56]:

"1274736 11/1989 Japan" should read --1-274736 11/1989 Japan--.

Figure 11:
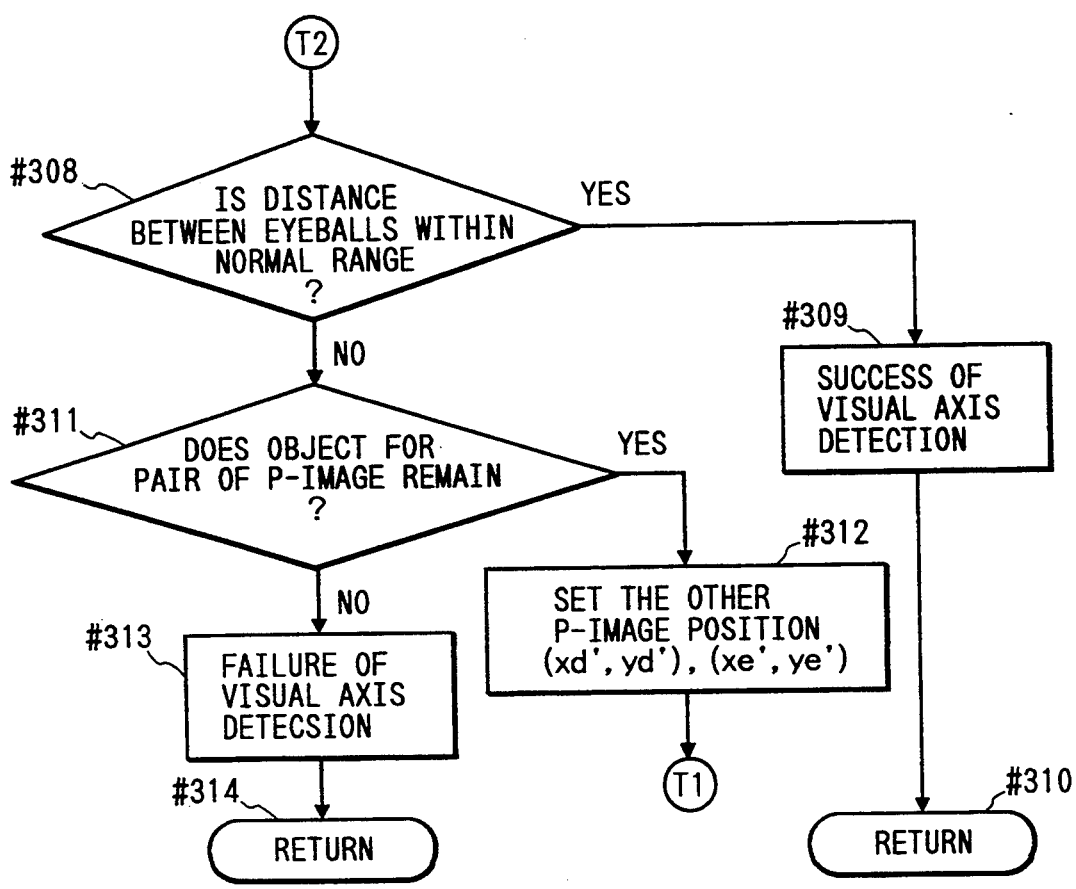
FIG. 11 is a flow chart of visual axis detection according to the present invention.

In the Drawings, sheet 10,

Figure 11, "DETECSION" should read --DETECTION--.

In the Drawings, sheet 11,

Figure 12, "DETECSION" should read --DETECTION--.

Column 3

Line 36, "express ions." should read --expressions.--.

Column 5

Line 25, "lense" should read --lens"--.

Column 7

Line 2, "points." should read --point.--,

Column 10

Line 13, "accomulation" should read --accumulation--; and
Line 36, "calelscence" should read --calescence--.

UNITED STATES PATENT AND TRADEMARK OFFICE
CERTIFICATE OF CORRECTION

PATENT NO. : 5,402,199
DATED : March 28, 1995
INVENTOR(S) : AKASHI, A.

It is certified that error appears in the above-indentified patent and that said Letters Patent is hereby corrected as shown below:

Column 12

Line 4, "angles" should read --angles of--; and
Line 35, "spacing A p" should read --spacing $\Delta p$--.

Column 13

Line 19, "flown" should read --flow--.

Column 14

Line 3, "relfected" should read --reflected--;
Lines 40, 41, "inappreciative" should read --inappropriate--; and
Line 55, "exhihiting" should read --exhibiting--.

Signed and Sealed this

Twenty-fifth Day of July, 1995

Attest:

BRUCE LEHMAN

*Attesting Officer*  *Commissioner of Patents and Trademarks*